(12) United States Patent
Knorth et al.

(10) Patent No.: US 11,944,712 B2
(45) Date of Patent: Apr. 2, 2024

(54) AIR GAP DEVICE AND LIQUID DISINFECTING CARTRIDGE COMPRISING THE AIR GAP DEVICE FOR A MEDICAL INSTRUMENT CLEANING AND DISINFECTING APPARATUS

(71) Applicant: Wassenburg Medical B.V., Dodewaard (NL)

(72) Inventors: Henny Hermanus Hendrik Knorth, Bemmel (NL); Ronald Wassenburg, Dodewaard (NL)

(73) Assignee: Wassenburg Medical B.V., Dodewaard (NL)

( * ) Notice: Subject to any disclaimer, the term of this patent is extended or adjusted under 35 U.S.C. 154(b) by 951 days.

(21) Appl. No.: 16/758,113

(22) PCT Filed: Oct. 26, 2018

(86) PCT No.: PCT/NL2018/050710
§ 371 (c)(1),
(2) Date: Apr. 22, 2020

(87) PCT Pub. No.: WO2019/083366
PCT Pub. Date: May 2, 2019

(65) Prior Publication Data
US 2020/0282094 A1    Sep. 10, 2020

(30) Foreign Application Priority Data
Oct. 27, 2017   (NL) ..................................... 2019820

(51) Int. Cl.
*A61L 2/18*    (2006.01)
*A61B 90/70*    (2016.01)
(Continued)

(52) U.S. Cl.
CPC .................. *A61L 2/18* (2013.01); *A61L 2/26* (2013.01); *A61B 90/70* (2016.02);
(Continued)

(58) Field of Classification Search
CPC .......... A61L 2/18; A61L 2/26; A61L 2202/17; A61L 2202/24; A61B 90/70
See application file for complete search history.

(56) References Cited

U.S. PATENT DOCUMENTS

| 5,678,592 A | 10/1997 | Boticki et al. |
| 2007/0240765 A1* | 10/2007 | Katzman ................. E03C 1/106 137/218 |
| 2016/0249794 A1 | 9/2016 | Suzuki |

FOREIGN PATENT DOCUMENTS

EP    1815782    8/2007

* cited by examiner

*Primary Examiner* — Sean E Conley
(74) *Attorney, Agent, or Firm* — Emerson, Thomson & Bennett, LLC; Roger D. Emerson; Matt J. Wilson

(57) ABSTRACT

The present invention relates to an air gap device for a medical instrument cleaning and disinfecting apparatus, the device comprising a housing having a first end adapted to allow liquid to enter the device and a second end adapted to discharge liquid from the device, wherein the first end comprises means for connecting the device to a disinfecting unit. The device further comprises handling means for handling the device. The present invention relates to a liquid disinfecting cartridge comprising the air gap device and the liquid disinfecting unit. Further, the present invention relates to a liquid disinfecting unit and air gap device intended for use in the liquid disinfecting cartridge and relates to an assembly of the medical instrument cleaning and disinfecting apparatus and the liquid disinfecting cartridge. The invention also relates to a method for interchangeably cou- (Continued)

Figure 1:
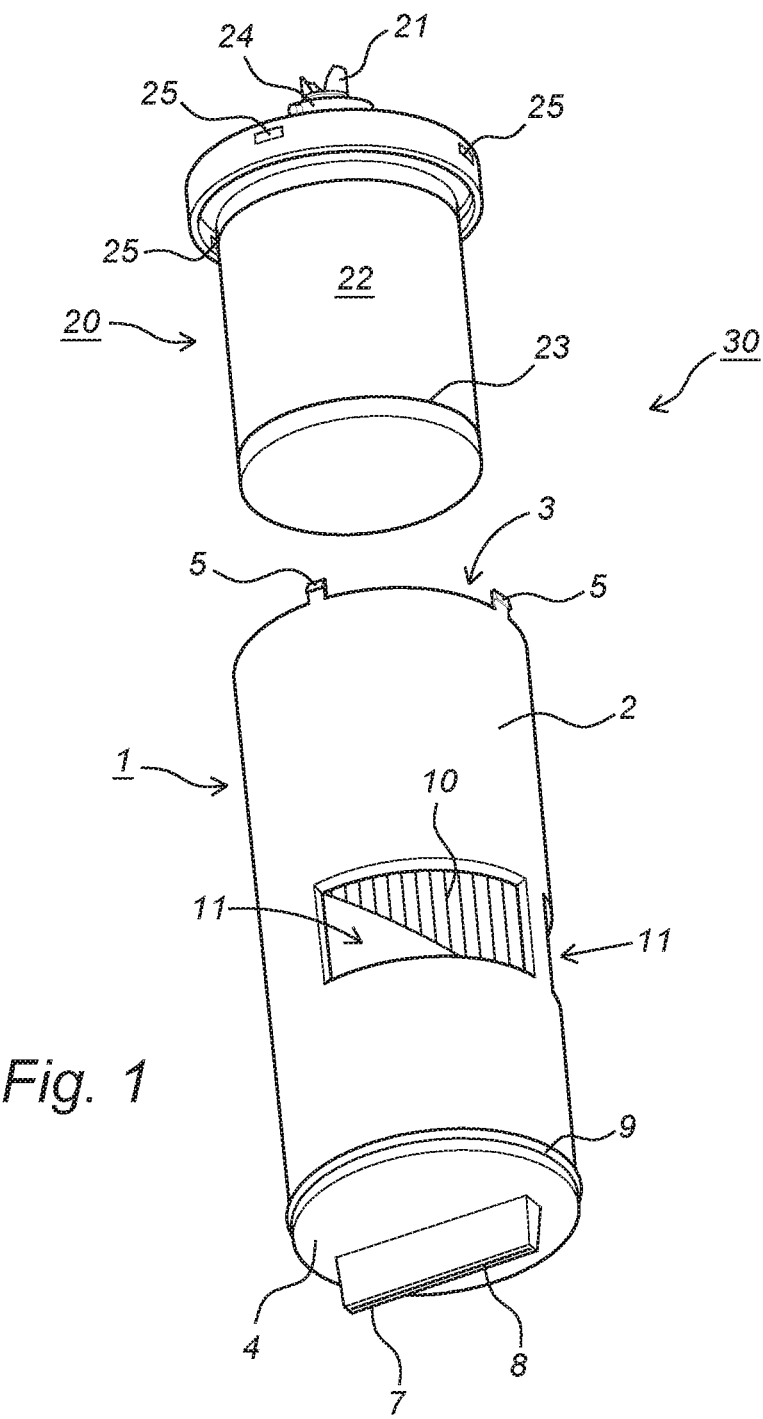

pling the liquid disinfecting cartridge with the medical instrument cleaning and disinfecting apparatus.

16 Claims, 5 Drawing Sheets

(51) Int. Cl.
*A61L 2/26* (2006.01)
*A61L 2/24* (2006.01)
(52) U.S. Cl.
CPC ........... *A61B 2090/701* (2016.02); *A61L 2/24* (2013.01); *A61L 2202/17* (2013.01); *A61L 2202/24* (2013.01)

AIR GAP DEVICE AND LIQUID DISINFECTING CARTRIDGE COMPRISING THE AIR GAP DEVICE FOR A MEDICAL INSTRUMENT CLEANING AND DISINFECTING APPARATUS

The present invention relates to an air gap device for a medical instrument cleaning and disinfecting apparatus, e.g. an endoscope washer disinfector apparatus. The present invention further relates to a liquid disinfecting cartridge comprising the air gap device of the present invention. The invention further relates to a liquid disinfecting unit and air gap device intended for use in the liquid disinfecting cartridge as well as an assembly of the medical instrument cleaning and disinfecting apparatus and the liquid disinfecting cartridge of the present invention. The present invention further relates to a method for interchangeably coupling the liquid disinfecting cartridge with the medical instrument cleaning and disinfecting apparatus.

Cleaning and disinfecting apparatuses for medical instruments, such as an endoscope washer disinfector apparatus, are widely used in the reprocessing (i.e. including the cleaning and disinfecting) of medical instruments. The reprocessing of medical instruments is a delicate and complex process, wherein contamination of the system must be avoided at all times. For medical instruments having narrow lumens and multiple internal channels, such as endoscopes, the cleaning and disinfecting process in particular is an even more complex and difficult task.

Medical instruments are usually highly contaminated with microorganisms, secretions, and blood during use. In particular for medical instruments having narrow lumens and multiple internal channels, bacteria are able to form biofilms on the inner channel surfaces, which can contribute to failure in the reprocessing of such instruments, e.g. endoscopes. To prevent cross-contamination due to any failure in the reprocessing of medical instruments to the minimum extend possible, many agencies have developed reprocessing guidelines.

In general, medical instrument reprocessing and, in particular, endoscope reprocessing includes pre-cleaning (at bedside), leak testing, manual cleaning, high-level disinfection, rinsing, drying, and storage. An automated reprocessor, e.g. an automated endoscope reprocessor, could be used to perform leak testing, washing, high-level disinfection, and to rinse the flexible endoscope. Still, manual cleaning before disinfection is necessary because flexible endoscopes can contain a high bio burden.

Lack of cleaning or failure during the cleaning process could lead to the survival of pathogens after disinfection, increasing the risk of cross-contamination between patients. In addition, bacteria that remain after insufficient reprocessing may form a biofilm inside the instruments.

The automated reprocessor, i.e. the cleaning and disinfecting apparatus for medical instruments, is supplied with tap water, which might potentially contaminate the reprocessing process even further. In order to avoid any additional contamination due to the use of tap water, the cleaning and disinfecting apparatus for medical instruments is typically provided with a liquid disinfecting unit for disinfecting the tap water before entering the reprocessing cycle. Such liquid disinfecting unit may be selected from a filter unit, e.g. a bacterial filter unit. The disinfected water is particularly used in the final rinse steps, to ensure a proper final clean of medical instruments prior to use.

To this purpose, the cleaning and disinfecting apparatus comprises a feed conduct for tap water which is connected by its first end to a tap for tap water and wherein the conduct is provided with a liquid disinfecting unit. The supplied liquid is thus disinfected by the liquid disinfecting unit before providing the liquid to the washer/disinfector. Such liquid disinfecting unit may be an integral part of the washer/disinfector but may also be a separated part of the washer/disinfector. The second end of the conduct is connected to an air gap to avoid contamination of the part of the conduct situated downstream the liquid disinfecting unit, i.e. the part situated between the liquid disinfecting unit and the second end of the conduct, by microorganisms present in the cleaning and disinfecting apparatus.

The liquid disinfecting unit is used repeatedly as long as the conditions for reuse of the liquid disinfecting unit are fulfilled, i.e. that the maximum reuse cycles is not exceeded and that the cleaning and disinfecting apparatus is in disinfected condition, or even sterile, before starting a new period of reprocessing (e.g. such a period may be defined as being a week or day). Although the present construction seems to work sufficient to disinfect contaminations from the supplied tap water, the part of the conduct situated downstream the liquid disinfecting unit is still vulnerable to contamination. Since the liquid flowing through the conduct situated downstream the liquid disinfecting unit is not further monitored on any form of contamination, any formation of biofilms on the inner surface of that specific conduct part will result in a non-avoidable failure in the reprocessing of medical instruments.

In order to improve the robustness and contamination controllability of the process of the reprocessing of medical instruments, the present invention provides in a first aspect an air gap device for a medical instrument cleaning and disinfecting apparatus, wherein the air gap device comprising a housing jacket defining two end surfaces: a first end surface adapted to allow liquid to enter the air gap device and a second end surface adapted to discharge liquid from the air gap device. The first end surface of the air gap device of the present invention comprises connecting means for connecting the air gap device to a liquid disinfecting unit comprising receiving means for receiving the connecting means of the air gap device. Further the housing jacket and/or the second end surface of the air gap device of the present invention optionally comprises handling means for handling the air gap device. By providing the air gap device of the present invention, the liquid disinfecting unit, in case connected to the air gap device, is forming an integral part of the liquid disinfecting unit—air gap assembly. In other words, by providing an air gap device according to the present invention, the liquid disinfecting unit is directly coupled to the air gap device avoiding any uncontrollable contamination of the feed conduct for tap water. Contamination of the liquid disinfecting unit by contaminations already present in the cleaning and disinfecting apparatus is prevented by the construction of the air gap device, whereas any contamination present in the feed conduct for tap water is disinfected by the liquid disinfecting unit before entering the air gap device. The air gap device of the present invention thus facilitates a reprocessing cycle wherein contamination of the process is further reduced. The connecting means may be configured to connect the air gap device to the liquid disinfecting unit in a detachable way. Detachable is consider to mean releasable, detachable or disconnectable. By providing a releasable, detachable or disconnectable connection between the liquid disinfecting unit and the air gap device of the present invention, the liquid disinfecting unit may be replaced by another liquid disinfecting unit without the need of replacing the air gap device as well and vice versa. Alternatively, the air gap device may be fixed, attached or permanently connected, such as welded to the liquid disinfecting unit, for instance by infrared welding.

The first end surface of the air gap device is typically arranged opposite the second end surface of the air gap device, wherein normally the first end surface is an upward side of the device, and the second end surface is a downward side of the device, such that liquid entering the device can flow under influence of gravity through the air gap device. In an embodiment the air gap device is substantially elongated or cylindrically shaped, and may be substantially arranged in a vertical, or mostly vertical direction. With mostly vertical is intended that the component of the orientation in vertical direction is larger than the component of the orientation in horizontal direction.

In order to facilitate the connection of the air gap device of the present invention with the liquid disinfecting unit, the first end surface may comprise an open end surface in order to enclose the liquid disinfecting unit. Preferably, the first end surface is adapted to enclose the liquid disinfecting unit at least partially. By providing a first end surface which is adapted to enclose the liquid disinfecting unit at least partially, the liquid disinfecting unit is still visible and accessible once connected to the air gap device. The accessibility of the liquid disinfecting unit facilitates the disassembling of a formed liquid disinfecting unit—air gap assembly.

In a preferred embodiment of the present invention, the connecting means of the air gap device are adapted to detachably connecting the air gap device to the liquid disinfecting unit, for example by providing connecting means comprising one or more snap-fit connectors. The snap-fit connectors may detachably cooperate with the receiving means of the liquid disinfecting unit. By providing a detachable connection between the liquid disinfecting unit and the air gap device of the present invention, the liquid disinfecting unit may be replaced by another liquid disinfecting unit without the need of replacing the air gap device as well.

The handling means of the air gap device may comprise gripping means, such as a grip connected to the second end surface, for gripping the air gap device by an operator. By providing handling means such as gripping means, the operator is able to grip the air gap in a predefined controllable way. Any contamination due to incorrect gripping of the device (before using the device in a reprocessing cycle) by the operator is thus further reduced. Preferably, any contact between the operator and the air gap device is prevented. Therefore, in a preferred embodiment the gripping means protrude from the second end surface to allow the operators hand to be situated at a certain distance from the air gap device.

Preferably the gripping means of the air gap device are provided with a discharge opening for discharging the liquid from the air gap device. Alternatively, the discharge opening may be situated in the second end surface. In such configuration the second end surface comprises at least one discharge opening for discharging the liquid from the air gap device. In general, the dimensions of the discharge opening are chosen such that the discharge opening provides a sufficient, i.e. meeting the requirements set by the cleaning and disinfecting apparatus, feed of liquid discharged from the air gap device. Further it was found that the dimensions of the discharge opening are chosen such that during loading and unloading of the basin of the washer/disinfector, the washer/disinfector is respectively vented and aerated. In addition, the dimensions of the discharge opening are chosen such that water from the washer/disinfector is prevented to enter the air gap device of the present invention.

In order to provide an airtight assembly of the air gap device of the present invention and the cleaning and disinfecting apparatus, the housing jacket comprises on its outer surface a sealing ring, wherein the sealing ring is adapted for co-action with an air gap receiving part of the cleaning and disinfecting apparatus. The air gap receiving part is typically situated right above the washer unit of a washer/disinfector apparatus. By providing a sealing ring, the air gap device may be airtight received by the cleaning and disinfecting apparatus, wherein the second end surface and the jacket surface between the second end surface and the sealing ring extends into the washer unit. Preferably, the handling means of the air gap device of the present invention are located on the part extending into the washer unit, i.e. located on the part of the air gap device defined by the second end surface and the jacket surface between the second end surface and the sealing ring. By providing the handling means on the washer unit extended part of the air gap device, the handling means are cleaned and disinfected during performance of the reprocessing cycle. Any cross-contamination by the handling means once the handling means are gripped by an operator is thus prevented. Also, any cross-contamination of the handling means caused by handling of the air gap device by an operator does not result in a failure in the reprocessing cycle, since the contaminated handling means are cleaned and disinfected during the cleaning and disinfecting of the medical instrument.

The housing jacket of the air gap device of the present invention may further comprise on its inner surface a liquid flow-blocking element, wherein the liquid flow-blocking element is adapted for co-action with a bottom part of the liquid disinfecting unit facing the air gap device. Such liquid flow-blocking element controls the flow of liquid discharged from the liquid disinfecting unit and flow through the air gap device. A liquid flow-blocking element is in particular preferred in case the housing jacket comprises at least one venting window for venting the air gap device of the present invention. The liquid flow-blocking element is configured such that any leakage of liquid from the air gap device via the at least one venting window is prevented.

The presence of a liquid flow-blocking element is not essentially located on the inner surface of the housing jacket of the air gap device; alternatively, a liquid disinfecting unit connected with the air gap may be provided with a flange located on at least a part of the circumferential edge of the bottom surface of the liquid disinfecting unit facing the air gap. In such embodiment, the flange of the liquid disinfecting unit controls the flow of liquid discharged from the liquid disinfecting unit and flow through the air gap device. In other words, such a flange of the liquid disinfecting unit then functions as a liquid flow-blocking element as described above.

In an embodiment of the present invention, the mutual minimal distance between the at least one venting window and the second end surface is at least 30 millimetres, preferably at least 40 millimetres. In particular, the mutual minimal distance between the at least one venting window and the second end surface is between 30 and 70 millimetres. Preferably the mutual minimal distance between the at least one venting window and the second end surface is between 40 and 60 millimetres. In a preferred embodiment, the mutual minimal distance is about 50 to 55 millimetres.

In a further embodiment of the present invention the first end surface is adapted to connect to the liquid disinfecting unit such that, the mutual minimal distance between the at least one venting window and a bottom side of the liquid disinfecting unit facing the air gap device is at least 4 millimetres. Preferably the mutual minimal distance between the at least one venting window and a bottom side of the liquid disinfecting unit facing the air gap device is about 6 to 8 millimetres.

The handling means of the air gap device of the present invention, may be located on the part of the air gap device defined by the second end surface and the jacket surface between the second end surface and the at least one venting window. As already provided above, the handling means are preferably located on the part of the air gap extending into the washer/disinfector to avoid any growth of biofilm on the air gap device due to cross-contamination by the handling of the air gap device by an operator, e.g. the operator's hand. Inherently, in an embodiment of the present invention, the sealing ring is located between the second end surface and the at least one venting window.

To avoid any leakage of liquid from the air gap device via the at least one venting window, the liquid flow-blocking element is preferably located between the first end surface and the at least one venting window. In a further preferred embodiment, the liquid flow-blocking element comprises a strip, and wherein at least a part of the length of the strip is located right above the at least one venting window. Such strip may be preferably made from a flexible material, e.g. flexible plastic or rubber, e.g. natural or synthetic rubber materials. The use of a flexible strip is in particular preferred to provide a form-fitting connection between the liquid flow-blocking element and a part of the liquid disinfecting unit. To control the flow of liquid through the air gap device, the liquid flow-blocking element preferably form-fittingly connects to the surface of the liquid disinfecting unit, which surface of the liquid disinfecting unit is the part of the surface defined between a discharge for discharging disinfected liquid from the liquid disinfecting unit and the bottom side of the liquid disinfecting unit.

The housing jacket of the air gap device of the present invention is preferably substantially cylindrical, even more preferred cylindrical. The air gap device may be made from any suitable material, however the air gap device made from plastic or stainless steel is preferred. By providing an air gap device made from plastic, the air gap device may be produced in a cost-efficient way resulting in an air gap device for single use, i.e. the use of the air gap device during the lifespan of the liquid disinfecting unit. By a single use air gap device, the air gap device is replaced together with the replacing of the liquid disinfecting unit by another liquid disinfecting unit. Alternatively, the air gap device may be made from stainless steel to provide an air gap device suitable for re-use. Preferably, the air gap device made from stainless steel may be cleaned and disinfected before reusing the air gap device.

In a second aspect, the present invention provides a liquid disinfecting cartridge for a medical instrument cleaning and disinfecting apparatus, wherein the liquid disinfecting cartridge comprises a liquid disinfecting unit connected to the air gap device of the present invention. The liquid disinfecting unit comprises an inlet for feeding a liquid, such as tap water, to the liquid disinfecting unit, a disinfecting filter adapted to disinfecting the liquid fed to the liquid disinfecting unit and a discharge for discharging the disinfected liquid from the liquid disinfecting unit. The liquid disinfecting unit of the liquid disinfecting cartridge of the present invention further comprises coupling means for interchangeably coupling the liquid disinfecting unit with a liquid disinfecting unit receiving part of the cleaning and disinfecting apparatus. By providing the coupling means, the liquid disinfecting cartridge can be easily coupled to a liquid disinfecting unit receiving part, preferably by gripping and holding the handling means of the air gap device for handling the liquid disinfecting cartridge.

In order to facilitate the easy coupling of the liquid disinfecting cartridge with the cleaning and disinfecting apparatus, the inlet of the liquid disinfecting unit is preferably adapted for co-action with a liquid supply of the cleaning and disinfecting apparatus. In order to facilitate a form-fittingly connection between the inlet of the liquid disinfecting unit and the liquid supply of the cleaning and disinfecting apparatus, the coupling means of the liquid disinfecting unit are preferably located adjacent to the inlet. The coupling means are preferably adapted for co-action with interlocking coupling means provided in the cleaning and disinfecting apparatus and may include coupling means adapted to provide a bayonet or threaded connection with the cleaning and disinfecting apparatus. Coupling mechanisms are preferred wherein the operator is able to replace the liquid disinfecting cartridge easily by another liquid disinfecting cartridge by an one hand-turn.

In a preferred embodiment of the present invention, the liquid disinfecting unit is connected to the first end surface of the air gap device such that the disinfecting filter of the liquid disinfecting unit is enclosed by the housing jacket of the air gap device. Even further, the liquid disinfecting unit is connected to the first end surface preferably such that an interstice is provided between the housing jacket of the air gap device and the disinfecting filter of the liquid disinfecting unit. In such embodiment, the liquid discharged from the filter may flow through the interstice into the air gap device. In an alternative embodiment, on the other hand, the liquid disinfecting unit may be provided with an interstice provided between the exterior wall of the cartridge and the disinfecting filter of the liquid disinfecting unit. In use, the liquid percolates from the interstice through the disinfecting filter into the air gap device.

In order to control and direct the flow of liquid through the interstice and the rest of the air gap device, at least the part of the interstice located right above the at least one venting window is preferably blocked by the liquid flow-blocking element provided on the inner surface of the jacket surface of the air gap device or by a flange located on at least a part of the circumferential edge of the bottom surface of the liquid disinfecting unit facing the air gap.

The liquid disinfecting cartridge of the present invention may further be provided with communication means, such as electronic communication means, e.g. RFID tags, to verify the status of the liquid disinfecting cartridge. Such verification may indicate whether the liquid disinfecting cartridge is suitable for use in the cleaning and disinfecting apparatus. For example, the electronic communication means may provide cartridge-specific data about the number of cycles still remaining before the cartridge has to be removed. Such measurement may be based on a predefined maximum number thermal self-disinfection cycles performed with the cartridge and/or a predefined lifetime of the cartridge (e.g. a day or a week). Further, the communication means may communicate whether the liquid disinfecting cartridge is correctly coupled with the cleaning and disinfecting apparatus.

In a third aspect, the present invention provides a liquid disinfecting unit and/or an air gap device intended for use in the liquid disinfecting cartridge of the present invention. The liquid disinfecting unit preferably comprises coupling means and/or receiving means.

In a fourth aspect, the present invention provides an air gap device intended for single-use in the liquid disinfecting cartridge of the present invention, wherein the air gap device is preferably made from plastic. Again, the term "single-use" refers to the use of the air gap device during the lifespan of the liquid disinfecting unit, i.e. the time one single liquid disinfecting unit is used during several reprocessing cycles. Alternatively, the present invention provides an air gap device intended for re-use in the liquid disinfecting cartridge of the present invention, wherein the air gap device is preferably made from stainless steel. The term "re-use" refers to the repeated use of the air gap device during the lifespan of multiple liquid disinfecting units. The term "re-use" may refer to the constant use of one single air gap device wherein in a continuous timeframe the air gap device is subsequently connected to multiple liquid disinfecting units. Also, the term "re-use" may refer to an intermittent use of one single air gap device wherein in between its use the air gap device is cleaned and disinfected.

In a fifth aspect, the present invention provides an assembly of a medical instrument cleaning and disinfecting apparatus and the liquid disinfecting cartridge of the present invention, wherein the liquid disinfecting cartridge is interchangeably coupled with the medical instrument cleaning and disinfecting apparatus.

In a preferred embodiment the liquid disinfecting cartridge of the present invention is coupled with the medical instrument cleaning and disinfecting apparatus at an angle with respect to the horizontal. The angle may be less than 90°, preferably about 80° to (although not including) 90°. Even more preferred the angle may be about 85°.

In a sixth aspect, the present invention provides a method for interchangeably coupling a liquid disinfecting cartridge with a medical instrument cleaning and disinfecting apparatus, comprising the steps of:
 a) providing the air gap device of the present invention;
 b) providing the liquid disinfecting unit as described above (third aspect);
 c) connecting the air gap device provided in step a) to the liquid disinfecting unit provided in step b) to form the liquid disinfecting cartridge of the present invention;
 d) gripping and holding the handling means of the liquid disinfecting cartridge; and
 e) coupling the liquid disinfecting cartridge with the medical instrument cleaning and disinfecting apparatus.

The method of the present invention thus facilitates the interchangeably coupling of a liquid disinfecting cartridge with a cleaning and disinfecting apparatus, by providing a robust and intuitive replacement method. The method of the present invention thus provides a way to efficiently replace the liquid disinfecting unit without running the risk of cross-contamination of any accessible part of the apparatus during replacement of the liquid disinfecting unit by an operator. It is noted that any cross-contamination might result in the growth of bacteria, e.g. by forming a biofilm, and failures in the reprocessing cycle due to contamination of the respective parts of the apparatus. By providing the method of the present invention the risk of cross-contamination is further reduced.

In a preferred embodiment of the method of the present invention, at least steps d) and e) may be performed manually by an operator. For example, in step e) the liquid disinfecting cartridge is preferably coupled with the medical instrument cleaning and disinfecting apparatus by an one hand-turn of the operator.

In a further embodiment of the method of the present invention, steps a)-c) are performed by the manufacturer of the liquid disinfecting cartridge before providing the liquid disinfecting cartridge to the end-user, e.g. the operator.

The method of the present invention may further comprising the step of f) removing the liquid disinfecting cartridge from the medical instrument cleaning and disinfecting apparatus by gripping and holding the handling means of the liquid disinfecting cartridge. Step f) may be performed manually by an operator. Inherently to step e), the liquid disinfecting cartridge in step f) may be removed from the medical instrument cleaning and disinfecting apparatus by an one hand-turn of the operator.

After removal of the liquid disinfecting cartridge from the medical instrument cleaning and disinfecting apparatus in step f), the method may further comprise the steps of:
 g) providing another liquid disinfecting unit;
 h) replacing the liquid disinfecting unit connected to the air gap device with the liquid disinfecting unit provided in step g); and
 i) recoupling the liquid disinfecting cartridge obtained in step h) with the medical instrument cleaning and disinfecting apparatus.

Figure 2:
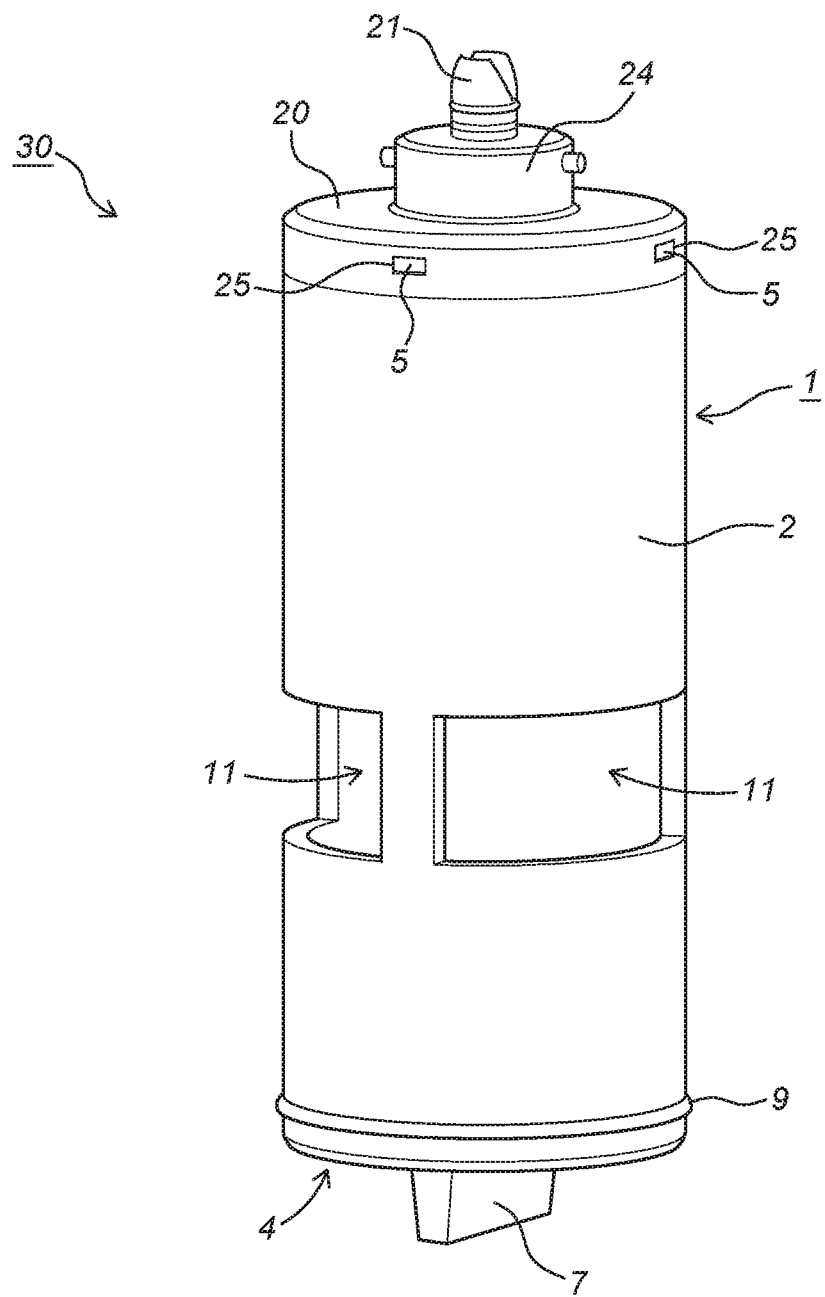
Figure 3:
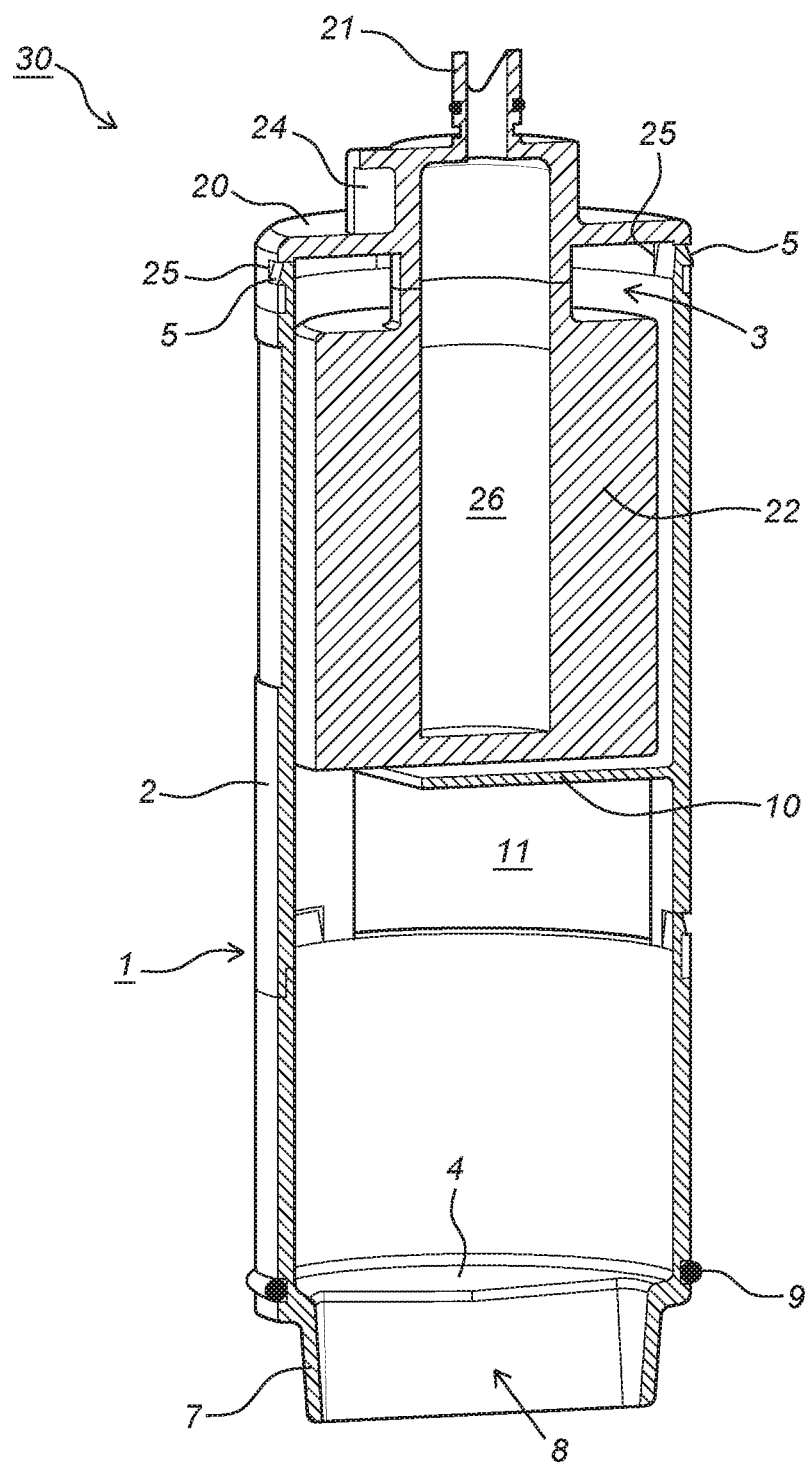
Figure 4A:
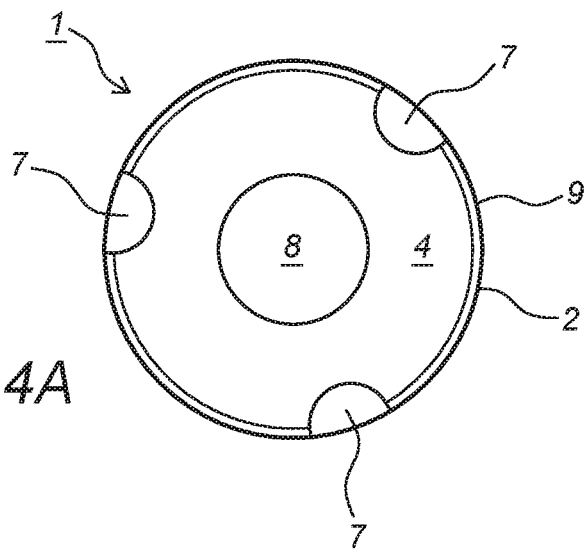
Figure 4B:
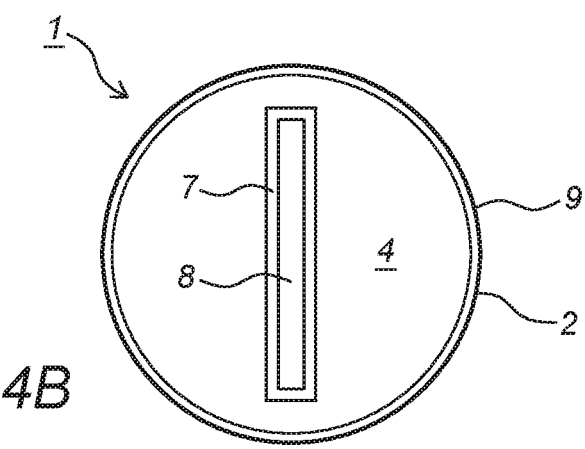
Figure 4C:
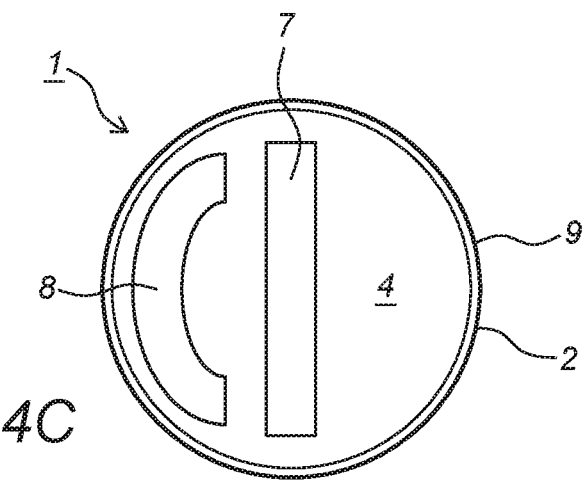
Figure 5:
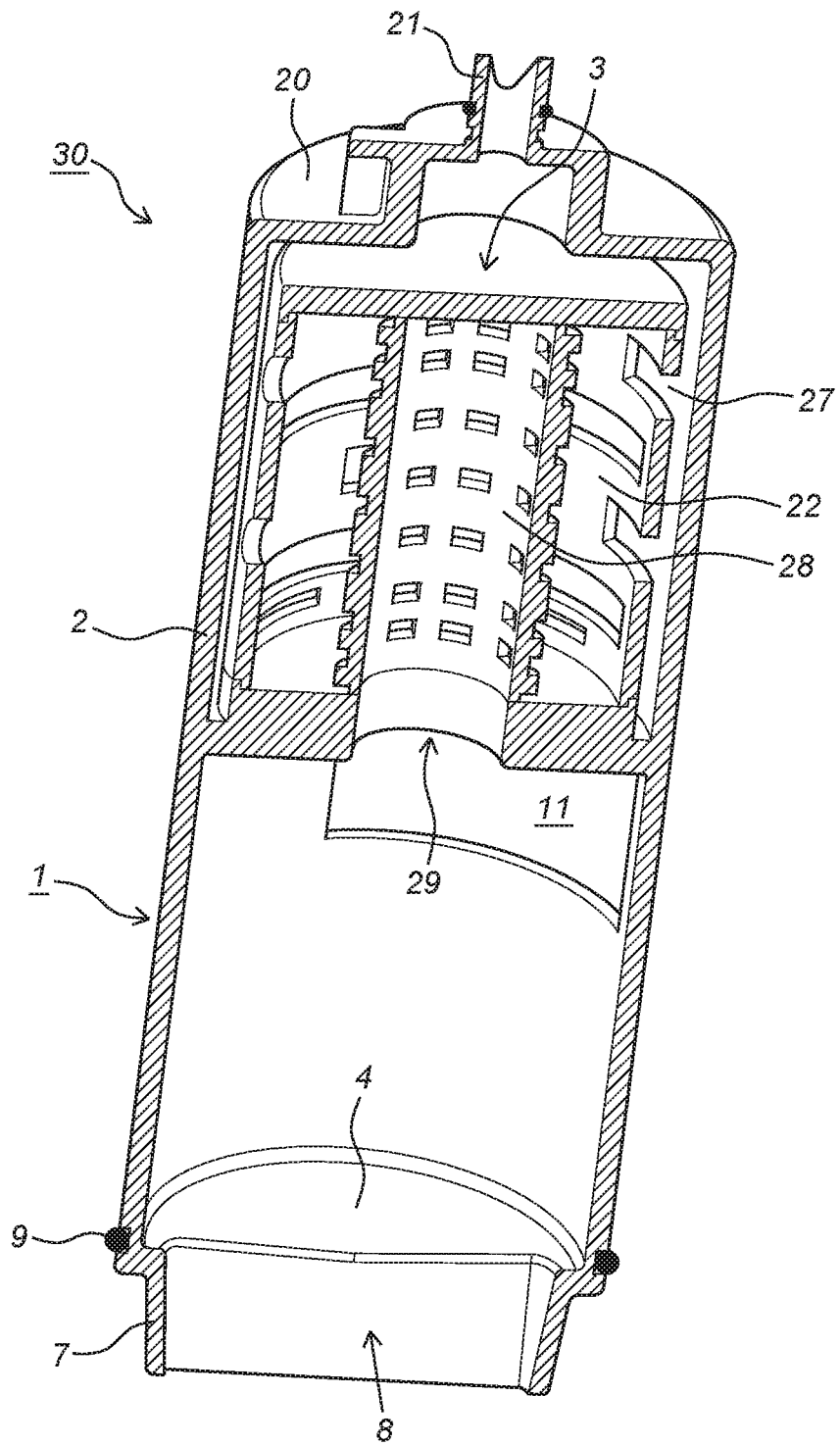

The present invention will be further elucidated on the basis of the non-limitative exemplary embodiments shown in the following figures. Herein shows:

FIG. 1 an exploded view of the liquid disinfecting cartridge according to the present invention;

FIG. 2 a perspective view of the liquid disinfecting cartridge according to the present invention;

FIG. 3 a cross sectional view of the liquid disinfecting cartridge according to the present invention;

FIG. 4A-C a bottom view of air cap device according to the present invention; and FIG. 5 a cross sectional view of the liquid disinfecting cartridge according to the present invention.

FIG. 1 shows an exploded view of the liquid disinfecting cartridge 30 of the present invention comprising the air gaps device 1 and a liquid disinfecting unit 20. The air gap device 1 comprises a housing jacket 2 which is substantially cylindrical having a first end surface 3 and a second end surface 4. The first end surface 3 comprises connecting means 5 for connecting the air gap device 1 to the liquid disinfecting unit 20 comprising receiving means 25 for receiving the connecting means 5 of the air gap device 1. The air gap device 1 further comprises handling means 7, here shown in the form of a grip protruding from the second end surface 4. The grip shown in FIG. 1 is provided with a discharge opening 8. The air gap device 1 is further provided with a sealing ring 9 situated between a venting window 11 and the second end surface 4. The air gap device 1 shown in FIG. 1 comprises two venting windows 11, The dimensions of the venting window 11 are chosen such that the air passing through the air gap device 1 complies with the requirements of the guidelines of healthcare agencies throughout the world, including water safety regulations, for example but not limited to the requirements laid down in BS EN1717:2000—*Protection against pollution of potable water in water installations and general requirements of devices to prevent pollution by backflow*. The inner surface of the housing jacket 2 is provided with a liquid flow-blocking element 10. In FIG. 1 the liquid flow-blocking element 10 is located such that any flow of liquid trough one of the venting windows 11 is prevented.

The liquid disinfecting unit 20 shown in FIG. 1 comprises an inlet 21, a disinfecting filter 22 and an discharge 23. Liquid supplied to the inlet 21 is disinfected by the disinfecting filter 22 and discharged from the discharge 23 to enter the air gap device 1 before being discharged from the discharge opening 8 of the air gap device 1. The liquid disinfecting unit 20 further comprises coupling means 24 for coupling the liquid disinfecting unit 20 with a liquid disinfecting unit receiving part of a cleaning and disinfecting apparatus (not shown).

FIG. 2 shows a perspective view of the liquid disinfecting cartridge 30 of the present invention. The liquid disinfecting cartridge 30 comprises the air gap device 1 connected to the liquid disinfecting unit 20 via a snap-fit connection by the connecting means 5 of the air gap device 1 and the receiving means 25 of the liquid disinfecting unit 20. FIG. 2 further shows the handling means 7 protruding from the second end surface 4, the sealing ring 9, two venting windows 11 and the inlet 21 of the liquid disinfecting unit 20. The inlet 21 of the liquid disinfecting unit 20 is provided with coupling means 24. In FIG. 2, the coupling means 24 are adapted to provide a bayonet connection with the cleaning and disinfecting apparatus (not shown).

FIG. 3 shows a cross-sectional view of the liquid disinfecting cartridge 30 of the present invention comprising the liquid disinfecting unit 20 coupled to the air gap device 1. In FIG. 3, the tap water will enter the liquid disinfecting unit 20 via inlet 21, which tap water will percolate from the central chamber 26 through the filter 22 into the air gap device 1.

FIG. 4A-C shows a bottom view of the air gap device 1 of the present invention. Several different configurations of the second end surface 4 are visualized, wherein each of the second end surfaces 4 shown comprises handling means 7, a discharge opening 8 and a sealing ring 9. The configuration of FIG. 4A deviates from the configurations shown in FIG. 4B and FIG. 4C in that the handling means 7 are provided circumferential edge of the second end surface and a part of the housing jacket 2. The handling means 7 are provided just below the sealing ring 9. The configuration of FIG. 4A provides a multi-finger grip. The multi-finger grip herewith allows a design of the second end surface 4 wherein the discharge opening 8 is located in the centre of the end surface 4.

The configuration of FIG. 4B deviates from the other configurations in that the discharge opening 8 is provided in the handling means 7. Although a central grip protruding from the second end surface 4 is preferred (as visualized in both FIG. 4B and FIG. 4C) the location of the discharge opening 8 may vary. Whereas in FIG. 4B the discharge opening 8 is provided in the grip, in FIG. 4C the discharge opening 8 is provided on one half of the second end surface 4. Due to the fact that the air gap device 1 is connected to the apparatus (not shown) at an angle with respect to the horizontal it might be beneficial, with regard to further reducing the contamination of the air gap device 1, to provide the discharge opening 8 at one half of the second end surface 4, i.e. the half of the second end surface 4 extending into the apparatus to a greater extent than the other half of the second end surface 4.

FIG. 5 shows a cross-sectional view of the liquid disinfecting cartridge 30 of the present invention comprising the liquid disinfecting unit 20 coupled to the air gap device 1. In FIG. 5, the tap water will enter the liquid disinfecting unit 20 via inlet 21, which tap water will percolate from the interstice 27 located between the exterior wall of the cartridge 30 and the filter 22 to a central chamber 28 through the filter 22 into the air gap device 1 via central opening 29. The diameter of the central opening 29 may be adjusted with adjustment means (not shown) to regulate the flow of liquid through the cartridge 30. It is noted that in the embodiment depicted in FIG. 5, the presence of a liquid flow-blocking element 10 (see: FIGS. 1 and 3) is no longer necessary. It is further noted that the liquid disinfecting unit 20 differs from the unit 20 depicted in FIG. 1, in that the unit 20 of FIG. 5 includes a substantial part of the exterior wall of the cartridge 30. The liquid disinfecting unit 20 of FIG. 5 comprises a filter unit 22 enclosed by a filter unit wall (forming a part of the exterior wall of the cartridge 30), wherein the interstice 27 is located in between the filter unit 22 and the filter unit wall.

The invention claimed is:

1. Air gap device (1) for a medical instrument cleaning and disinfecting apparatus, the air gap device (1) comprising a housing jacket (2), wherein the housing jacket (2) defines two end surfaces (3, 4):
   a first end surface (3) adapted to allow liquid to enter the air gap device (1); and
   a second end surface (4) adapted to discharge liquid from the air gap device (1), wherein the first end surface (3) comprises connecting means (5) for connecting the air gap device (1) to a liquid disinfecting unit (20) comprising receiving means (25) for receiving the connecting means (5) of the air gap device (1), and in that the housing jacket (2) and/or the second end surface (4) comprises handling means (7) for handling the air gap device (1), wherein the first end surface (3) of the housing jacket (2) is arranged opposite the second end surface (4) of the housing jacket (2).

2. Air gap device (1) according to claim 1, wherein the first end surface (3) is adapted to enclose the liquid disinfecting unit (20) at least partially, and/or wherein the first end surface (3) comprises an open end surface.

3. Air gap device (1) according to claim 1, wherein the connecting means (5) comprise one or more snap-fit connectors.

4. Air gap device (1) according to claim 1, wherein the handling means (7) comprise gripping means, such as a grip connected to the second end surface (4), for gripping the air gap device (1) by an operator, wherein the gripping means protrude from the second end surface (4) and/or wherein preferably the gripping means are provided with a discharge opening (8) for discharging the liquid from the air gap device (1).

5. Air gap device (1) according to claim 1, wherein the second end surface (4) comprises at least one discharge opening (8) for discharging the liquid from the air gap device (1) and/or wherein the housing jacket (2) comprises on its outer surface a sealing ring (9), wherein the sealing ring (9) is adapted for co-action with an air gap receiving part of the cleaning and disinfecting apparatus.

6. Air gap device (1) according to claim 5, wherein the handling means (7) are located on the part of the air gap device (1) defined by the second end surface (4) and the jacket surface between the second end surface (4) and the sealing ring (9).

7. Air gap device (1) according to claim 1, wherein the housing jacket (2) comprises on its inner surface a liquid flow-blocking element (10), wherein the liquid flow-blocking element (10) is adapted for co-action with a bottom part of the liquid disinfecting unit (20) facing the air gap device (1) and/or wherein the housing jacket (2) comprises at least one venting window (11) for venting the air gap device (1), wherein the mutual minimal distance between the at least one venting window (11) and the second end surface (4) is at least 30 millimeters.

8. Air gap device (1) according to claim 7, wherein the first end surface (3) is adapted to connect to the liquid disinfecting unit (20) such that, the mutual minimal distance between the at least one venting window (11) and a bottom side of the liquid disinfecting unit (20) facing the air gap device (1) is not more than 10 millimeters.

9. Air gap device (1) according to claim 7 wherein the handling means (7) are located on the part of the air gap device (1) defined by the second end surface (4) and the jacket surface between the second end surface (4) and the at least one venting window (11), and/or wherein the sealing ring (9) is located between the second end surface (4) and the at least one venting window (11).

10. Air gap device (1) according to claim 7, wherein the liquid flow-blocking element (10) is located between the first end surface (3) and the at least one venting window (11), wherein the liquid flow-blocking element (10) comprises a strip, and wherein at least a part of the length of the strip is located right above the at least one venting window (11).

11. Air gap device (1) according to claim 1, wherein the housing jacket (2) is substantially cylindrical.

12. A medical instrument cleaning and disinfecting apparatus, comprising:
   a liquid disinfecting cartridge (30) comprising:
      a liquid disinfecting unit (20), wherein the liquid disinfecting unit (20) comprises:
         an inlet (21) for feeding a liquid to the liquid disinfecting unit (20);
         a disinfecting filter (22) adapted to disinfect the liquid fed to the liquid disinfecting unit (20); and
         a discharge (23) for discharging the disinfected liquid from the liquid disinfecting unit (20),
      an air gap device (1) for a medical instrument cleaning and disinfecting apparatus, the air gap device (1) comprising a housing jacket (2), wherein the housing jacket (2) defines two end surfaces (3, 4):
         a first end surface (3) adapted to allow liquid to enter the air gap device (1); and
         a second end surface (4) adapted to discharge liquid from the air gap device (1),
      wherein the first end surface (3) comprises connecting means (5) for connecting the air gap device (1) to the liquid disinfecting unit (20) comprising receiving means (25) for receiving the connecting means (5) of the air gap device (1), and in that the housing jacket (2) and/or the second end surface (4) comprises handling means (7) for handling the air gap device (1), wherein the first end surface (3) of the housing jacket (2) is arranged opposite the second end surface (4) of the housing jacket (2);
      wherein the liquid disinfecting unit (20) further comprises coupling means (24) for interchangeably coupling the liquid disinfecting unit (20) with a liquid disinfecting unit receiving part of the cleaning and disinfecting apparatus, and in that the liquid disinfecting unit (20) is connected to an air gap device (1).

13. A medical instrument cleaning and disinfecting apparatus according to claim 12, wherein the inlet (21) is adapted for co-action with a liquid supply of the cleaning and disinfecting apparatus, and/or wherein the coupling means (24) are located adjacent to the inlet (21).

14. A medical instrument cleaning and disinfecting apparatus according to claim 12, wherein the coupling means (24) are adapted for co-action with interlocking coupling means provided in the cleaning and disinfecting apparatus, and/or wherein the coupling means (24) are adapted to provide a bayonet or threaded connection with the cleaning and disinfecting apparatus.

15. A medical instrument cleaning and disinfecting apparatus according claim 12, wherein the liquid disinfecting unit (20) is connected to the first end surface (3) of the air gap device (1) such that the disinfecting filter (22) of the liquid disinfecting unit (20) is enclosed by the housing jacket (2) of the air gap device (1), wherein the liquid disinfecting unit (20) is connected to the first end surface (3) such that an interstice is provided between the housing jacket (2) of the air gap device (1) and the disinfecting filter (22) of the liquid disinfecting unit (20) and/or wherein at least the part of the interstice located right above the at least one venting window (11) is blocked by a liquid flow-blocking element (10) provided on the inner surface of the jacket surface of the air gap device (1) or by a flange located on at least a part of the circumferential edge of the bottom surface of the liquid disinfecting unit (20) facing the air gap.

16. Assembly of a medical instrument cleaning and disinfecting apparatus and the liquid disinfecting cartridge (30) according to claim 12, wherein the liquid disinfecting cartridge (30) is interchangeably coupled with the medical instrument cleaning and disinfecting apparatus, wherein preferably the liquid disinfecting cartridge (30) is coupled with the medical instrument cleaning and disinfecting apparatus at an angle with respect to the horizontal, wherein the angle is less than 90°.

\* \* \* \* \*